United States Patent [19]
Brinkmann

[11] Patent Number: 5,805,622
[45] Date of Patent: Sep. 8, 1998

[54] APPARATUS FOR THE GENERATION OF LASER PULSES IN THE US-TIME RANGE

[75] Inventor: Ralf Brinkmann, Lübeck, Germany

[73] Assignee: Medizinisches Laserzentrum Lübeck GmbH, Lubeck, Germany

[21] Appl. No.: 827,711

[22] Filed: Apr. 8, 1997

Related U.S. Application Data

[63] Continuation of Ser. No. 377,222, Jan. 24, 1995, abandoned.

[30] Foreign Application Priority Data

Jan. 24, 1994 [DE] Germany .................. 44 01 917.3

[51] Int. Cl.$^6$ .................................................. H01S 3/10
[52] U.S. Cl. .................. 372/9; 372/23; 372/22; 372/10; 372/4; 372/5
[58] Field of Search ................... 372/38, 13, 22, 372/25, 31, 26, 11, 30, 97, 10, 4, 5

[56] References Cited

U.S. PATENT DOCUMENTS

| | | | |
|---|---|---|---|
| 5,272,713 | 12/1993 | Sobey et al. | 372/97 |
| 5,303,250 | 4/1994 | Masuda et al. | 372/22 |
| 5,339,323 | 8/1994 | Hunter et al. | 372/25 |
| 5,390,204 | 2/1995 | Yessik et al. | 372/25 |

*Primary Examiner*—Leon Scott, Jr.
*Attorney, Agent, or Firm*—Antonelli, Terry, Stout & Kraus, LLP

[57] ABSTRACT

Disclosed is an apparatus for generating laser pulses, which has a Q-switched solid state laser and at least one nonlinear crystal, and the application of this apparatus for removing material in the biomedical field. The present invention is distinguished by the nonlinear crystal being disposed inside the resonator of the solid state laser and by a pulse prolongation unit determining the pulse form and duration of the light pulse developing in the resonator.

22 Claims, 3 Drawing Sheets

APPARATUS FOR THE GENERATION OF LASER PULSES IN THE US-TIME RANGE

This application is a continuation application of Ser. No. 08/377,222, filed Jan. 24, 1995, now abandoned.

BACKGROUND OF THE INVENTION

The present invention relates to an apparatus for the generation of laser pulses, which has a Q-switched solid state laser and at least one nonlinear crystal.

Laser systems, in the beam path of which nonlinear crystals are integrated, are usually operated with the intention of multiplying the frequencies of the light waves generated by the laser system. Thus, it has been known for some time that, by way of illustration, the frequencies of laser pulses of a specific wavelength can be doubled by disposing nonlinear crystals in the beam path outside the resonator. In this way, the conversion efficiency of the nonlinear crystal is however restricted and becomes increasingly smaller the longer the pulses last, because the conversion efficiency rises in proportion to the intensity of the irradiation. Therefore, as short as possible laser pulses are advantageous for multiplying the frequency in order to convert a large as possible radiation portion of the fundamental wavelength. For this reason, the known Q-switch technique has been employed for the production of as short as possible laser pulses since the 1960s.

In contrast to the aforementioned object of generating laser pulses as short as possible, there are applications in which the frequency-multiplied laser pulses of as long as possible pulse duration are of great interest. As an example therefor, light pulse transmission via quarz fibers is mentioned which, depending on their dimensions, can only transmit limited "light energy packages" without being damaged themselves. In particular, the prolongation of Q-switch laser pulses has hitherto been only rarely of interest as the Q-switch technique is chiefly utilized for shortening laser pulses.

The operation of flashlamp pumped solid state lasers has the disadvantage that all the optical elements located in the laser system have so-called "spikes" which can damage the optical elements depending on the pulse power. As early as the 1960s, nonlinear absorbing media were therefore disposed inside the resonator of a ruby laser in order to dampen or entirely prevent the aforementioned "spikes", i.e., the spontaneously occuring pulse power peaks of the laser.

Furthermore, it is known that the use of nonlinear crystals inside the resonator can contribute to pulse prolongation, insofar as the nonlinear crystal is oriented at a suited angle position to the polarization plane of the fundamental wave. (see hereto "ein µs Alexandrite Laser für laserinduzierte Schockwellenlithotripsie", Laser und Optoelektronik 21(6) /1989, pp. 56–61).

If on the other hand, the generation of light pulses in the range of long pulse duration is the object, by way of illustration in the µs-range, another method of forming pulses is suggested in the aforementioned printed publication. A substantial improvement regarding the control of the pulse form is achieved by electronically controlling resonator losses with the aid of a, by way of illustration, resonator-internal Pockels cell. The feedback coupling of the emitted laser radiation serves as the control signal for controlling. However, it must be possible to conduct the electronic control of the resonator losses within one pulse emission. This is, by way of illustration, possible by regulating the high voltage of a resonator-internal Pockels or Kerr cell.

Thus, high demands are made on a control circuit of this type. During the leading edge of a Q-switch pulse, voltages of several kV have to be applied to the Pockels cell in order to dampen the laser pulse already at its leading edge. Other embodiments thereof can be found in the aforementioned text site.

Depending on the laser application, the parameterization of the laser system has to be reconducted anew in compliance with the general conditions.

Thus, in the field of material processing and removal by means of laser light, exacting demands are made on the light power which permits processing of this type in the first place, on the one hand, and on the application optics guiding the light generated in the laser system to the site of the material processing on the other. This presupposes that the light energy is usually guided via quarz glass fibers is not too high so that the quarz glass fibers are not damaged due to high pulse power but also are not too low in order to permit material processing.

SUMMARY OF THE INVENTION

The object of the present invention is to design an apparatus for generating laser pulses having a Q-switched solid state laser and at least one nonlinear crystal in such a manner that the laser pulses can be utilized in the field of material processing respectively removal and can be safely transmitted with as high as possible pulse energy via quarz glass fibers. In particular, removal of tissue in the medical field is to be conducted with the aid of the present apparatus.

A solution to the object forming the basis of the present invention is set forth in claims 1 and 15 hereto. Further, advantageously designed features of the present invention are contained in claims 2 to 14 as well as in claims 16 to 18.

A key element of the present invention is that the apparatus for generating laser pulses having a Q-switch solid state laser and at least one nonlinear crystal is distinguished by the nonlinear crystal being disposed inside the resonator of the solid state laser and that a pulse prolongation unit determines the pulse form and duration of the light pulses developing in the resonator. By this means it is attained one that the frequencies of the light pulses of the fundamental wave generated by the solid state laser are doubled and two that the light pulses are prolonged by the nonlinear crystal as well as by the pulse prolongation unit connected to the resonator in such a manner that they lie in the µs time range permitting safe transmission via the quarz glasss fiber to the site where, by way of illustration material processing occurs.

Thus, the high power density in the resoator required for UV-pulse conversion is attained by the resonators losses being to a major part generated by the frequency conversion and the decoupling losses for the fundamental wavelength being held low. Due to the nonlinear characteristic of doubling the frequency, high power densities in the resonator are limited by the doubling itself so that in the case of an optimum layout of the system, damage due to high power cannot occur.

An element of the present invention is that for pulse prolongation the nonlinear behavior of the crystal disposed inside the resonator is utilized, which crystal effects a pulse prolongation of approximately by the factors 2 or 3, as well as the laser pulse forming properties of an optical element which is also integrated inside the resonator and which is preferably a Pockels cell, which is activated by means of high voltage from a pulse prolongation unit. In this way, according to the present invention laser pulses in the µs-range which are composed of the fundamental wave and, by way of illustration, of the second harmonic wave are generated. Depending on the application, both laser wavelengths can be utilized singly or in combination.

The pulse prolongation unit is activated by laser light, which itself originates from the laser system in an as such known manner. A conversion of the light energy into electric high voltage signals which are applied to the inputs of the the Pockels cell occurs. In this way, an active control of the Pockels cells is created in dependence on the light pulses developing in-side the resonator.

Furthermore, the Pockels cell can simultaneously also be employed as an optical switch for the Q-switch circuit which activates the Pockels cell separately from the pulse prolongation unit.

If on the other hand a passive Q-switch solution is preferred, by way of example by means of a passive absorber (dye), a Pockels cell respectively a Kerr cell or an equivalent optical element is still required for active pulse prolongation.

The disposal of the nonlinear crystal inside the resonator area, inside which the doubled wavelength can develop and propagate unhindered by the active medium has proven to be very advantageous. This can be achieved by the nonlinear crystal being disposed between the end mirror of the resonator and a wavelength-selective mirror which simultaneously is the exit mirror for the frequency doubled wavelength.

Another element of the present invention is that is was recognized that the generation of UV laser pulses having $\mu$s-pulse duration is especially suited for material processing and removal of biological tissue. In particular, in the field of angioplasty, which is concerned with the removal of deposits in the blood vessels, laser systems are needed that generate laser pulses of a specific energy in the UV-range. Generation of $\mu$s-laser pulses are especially advantageous for the safe transmission via quarz glass fibers although large amounts of energy can be transmitted.

The present invention is made more apparent by way of example in the following without the intention of limiting the scope or spirit of the inventive idea using preferred embodiments with reference to the accompanying drawings to which moreover reference is explicity made for the disclosure of the invented details not further explained herein. Depicted are:

DESCRIPTION OF THE PREFERRED EMBODIMENT(S)

Figure 1:
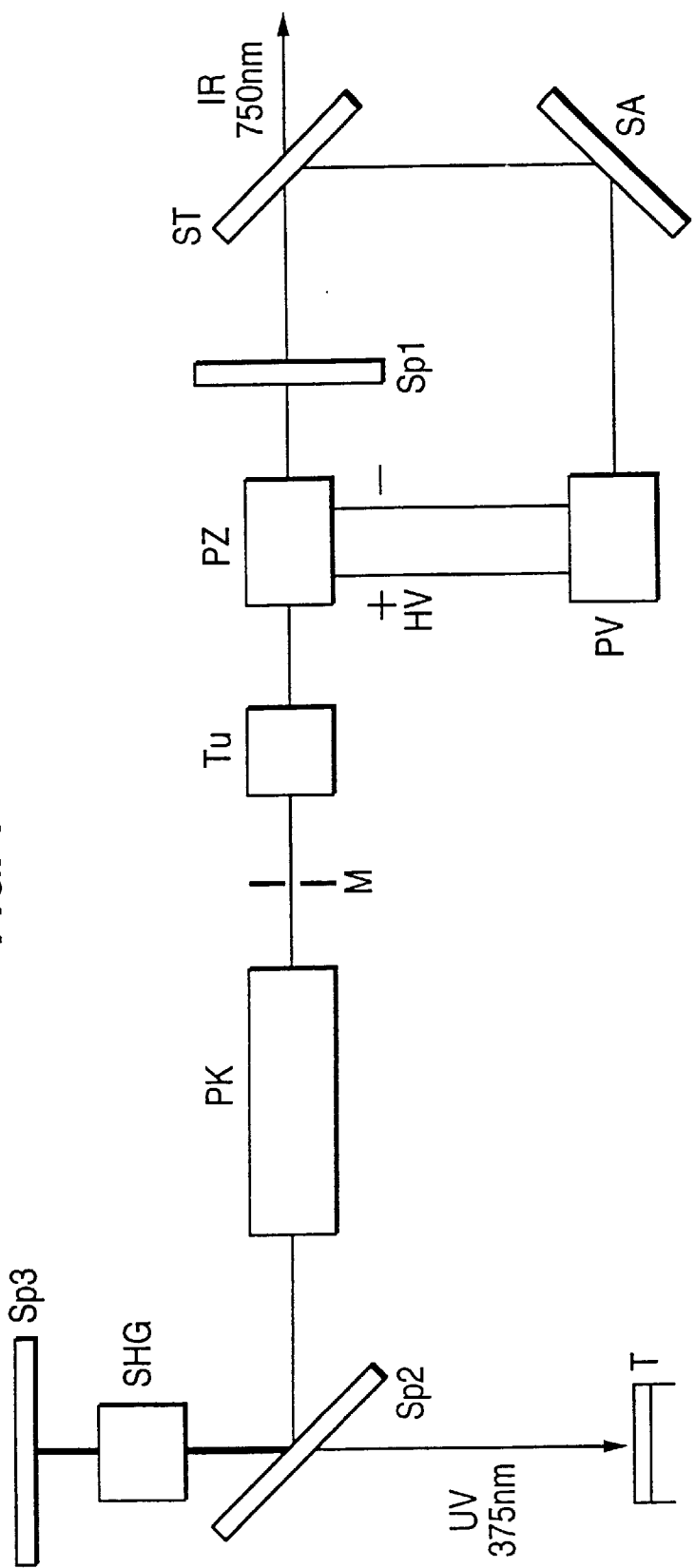
FIG. 1 shows a solid state laser having frequency-doubled irradiation in the $\mu$s-time range.

FIG. 1 shows an invented embodiment that is principally provided with a so-callled folded laser resonator, the end mirrors of which are designated Sp3 and Sp1. The other so-called deflection mirror Sp2 folds the beam path given here into two resonators halves which are perpendicular to each other. The experimental buildup depicted in FIG. 1 is an alexandrite laser whose pump chamber PK pumped with flash lamps generates, within the given resonator, light pulses which have an original pulse duration of approximately 100 ns and a wavelength of 750 nm. The use of a nonlinear crystal SHG (second harmonic generation) which is disposed isolated in one resonator half permits generation of the second harmonic wave so that in the given case a wavelength of 375 nm is created. In addition to the pump chamber PK, which is provided in the second resonator half, the latter also has a mode aperture M as well as a wavelength selector (tuner) TU which compresses the bandwidth of the fundamental radiation. The mode aperture M provides for the selection of transversal modes.

In this way, a laser resonator is created which generates two wavelenghts simultaneously which may emerge from the system at various sites in dependence on the provided Q-switch mirrors. Therefore, the deflection mirror Sp2 is coated in such a manner that it lets the ultraviolet beam portion pass, whereas the fundamental wave is reflected by it. The end mirror Sp1, on the other hand, constitutes a semi-reflecting mirror for the fundamental wavelength so that the latter can pass the mirror at least with a specific percentage of its radiation portion.

Furthermore, the embodiment according to FIG. 1 is provided with a pulse prolongation unit PV which is hit via the beam splitter ST and another deflection mirror SA by the fundamental wave leaving the laser system. The pulse prolongation unit PV converts these optical signals into electric activation signals which are applied to an optical element integrated inside the resonator. In the embodiment depicted in FIG. 1, the optical element is a Pockels cell PZ serving as the aimed-at variation of the resonator Q. In the present case, the Q-switch of the laser resonator is composed of the Pockels cell PZ which is at the same time connected to the pulse prolongation unit PV. In this way, the Pockels cell PZ has two functions.

In contrast to it, an embodiment is possible which is provided with a passive switch, by way of illustration a saturable absorber as the Q-switch. In this event, in addition, a Pockels cell would be provided an extra arrangement for the pulse prolongation unit.

Figure 2A:
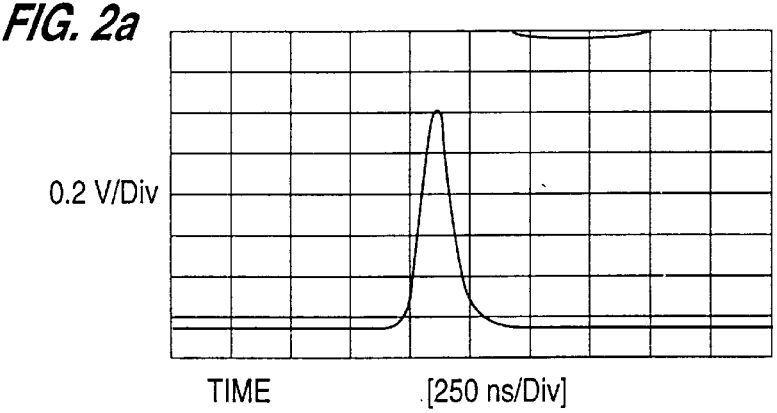
FIG. 2a shows a time representation of the pulse form of the fundamental wave pulse.
Figure 2B:
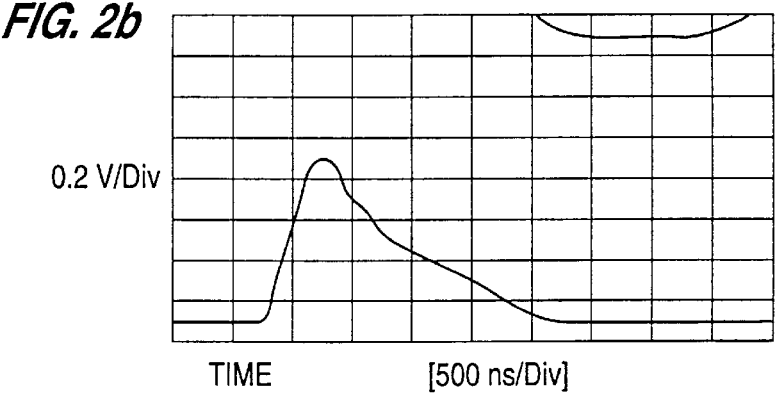
FIG. 2b shows a time representation of the pulse form with disposal of the nonlinear crystal inside the resonator.

In FIG. 2a, which must be seen compared to FIG. 2b, the pulse form is depicted in a time diagram corresponding to the pulse of the fundamental wavelength not connected to a nonlinear crystal as well as not connected to the pulse prolongation unit. In FIG. 2b, in contrast thereto, the course of the pulse is depicted with the crystal connected. In this way, the pulse duration could be prolonged from approximately 150 ns(see FIG. 2a) to 1 $\mu$s (see FIG. 2b therefor).

Figure 3:
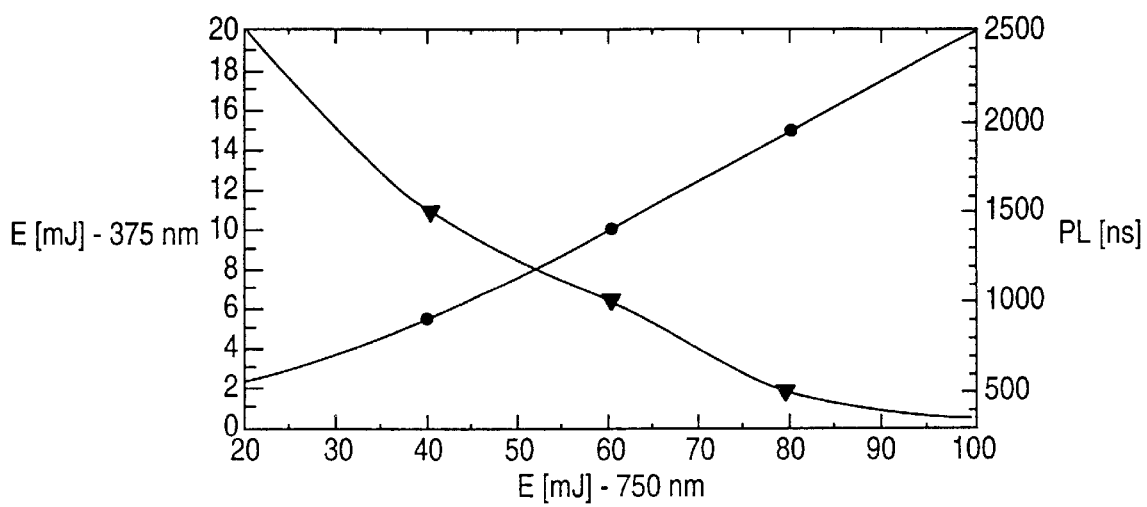
FIG. 3 shows the dependency of the UV-energies generated with the invented system on the pulse length as well as on the pump energies.

FIG. 3 shows the course of the pulse length and pulse energy of the doubled radiation portion as the function of the fundamental energy (see absciss values) decoupled through the mirror Sp1. The energy units of the doubled wavelength are plotted on the left ordinate and the pulse lengths PL are plotted on the right ordinate. The graph with the triangles shows the functional relationship between the energy of the fundamental wavelength and pulse length. On the other hand, the course in the diagram with the dots shows the relationship between the pump energy and the energy that can be generated in the doubled frequency range. The measured results depicted in FIG. 3 were won when not connected to the pulse prolongation unit. It turned out that the pulse energies can be generated in the doubled frequency range of approximately 20 mJ with a pump power of 100 mJ and a pulse duration of 350 ns.

Figure 4A:
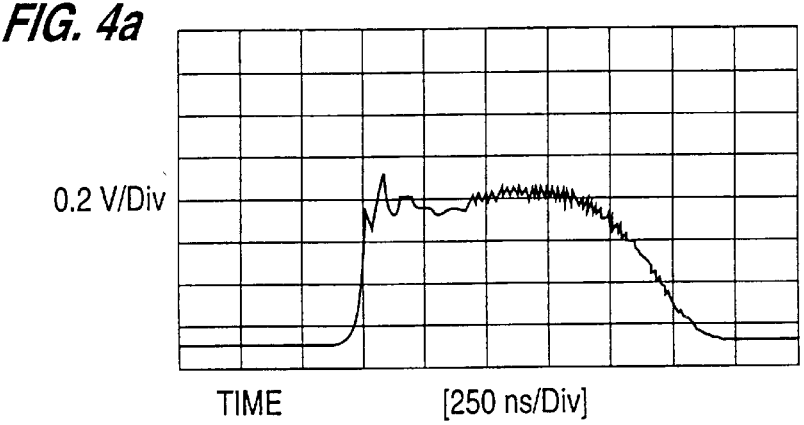
FIG. 4a shows a time representation of the pulse form of the fundamental wave by means of a pulse prolongation unit.
Figure 4B:
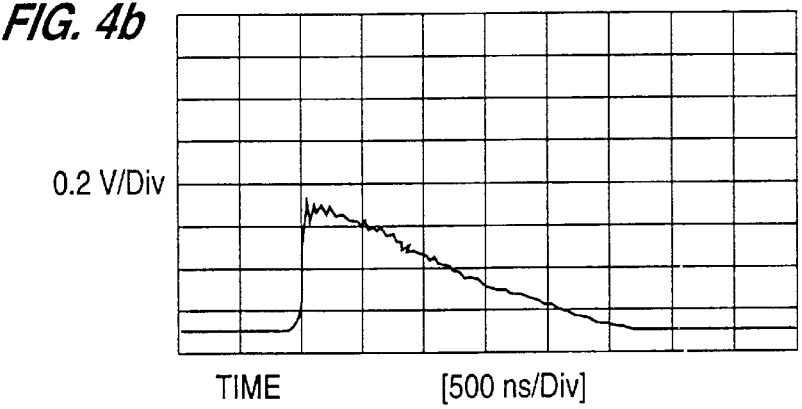
FIG. 4b shows a time representation of the pulse form by means of a nonlinear crystal and a pulse prolongation unit.

In comparison thereto, FIGS. 4a and 4b each show pulse forms with a connected pulse prolongation unit, with the fundamental laser pulse being depicted in FIG. 4a without the influence of the crystal and in FIG. 4b with the crystal being connected. It can be seen that the pulse duration remains practically unchanged due to the connected pulse prolongation unit but nonetheless the nonlinear crystal exerts considerable change on the respective pulse form.

Figure 5:
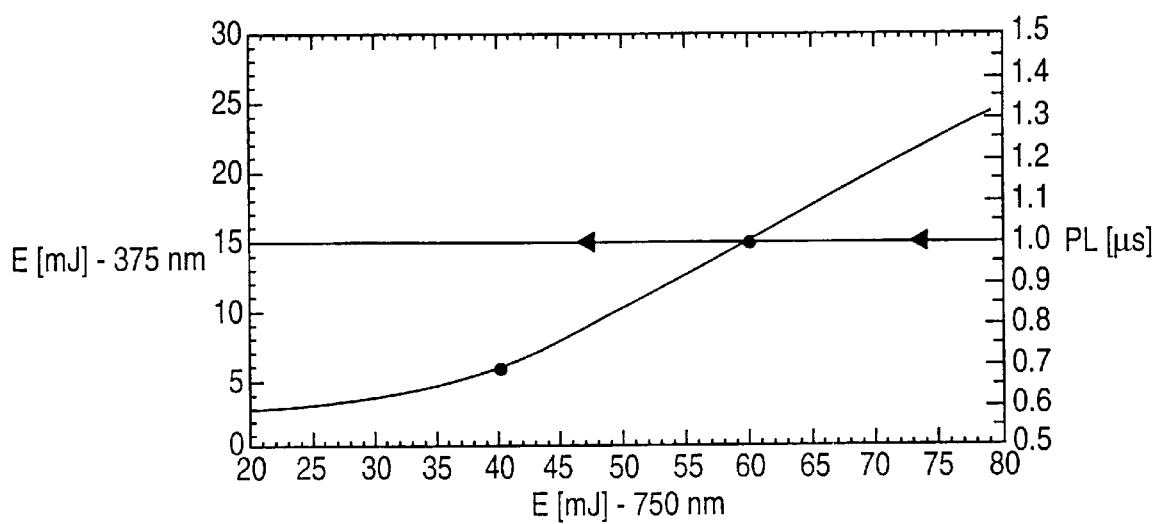
FIG. 5 shows UV-energy dependency on the pump energy and on the pulse length.

FIG. 5 shows once more the functional relationship between the pump power of the fundamental wavelength as well as the energy of the doubled frequency in dependence on the pulse length set constant (the graph with the triangles shows the pulse length of the light pulses;the graph with the dots shows the energy relationship between the pump energy and UV-energy). It turned out that with the integration of the crystal and the pulse prolongation unit inside the resonator, the energies that can be generated with double frequency are distinctly higher than is the case in the described instance according to FIG. 3. Furthermore, the given pulse length of 1 $\mu$s permits safe transmission of light pulses having the doubled frequency via quarz glass fibers.

What is claimed is:

1. An apparatus for the generation of laser pulses with pulse durations in a range of $\mu$-seconds, comprising:
   a Q-switched solid state laser having a O-switch and end mirrors defining resonator cavity for generation of a laser beam, wherein at least one mirror of said end mirrors is a dielectric mirror through which at least laser pulses of a laser beam are transmitted therethrough;
   a pulse prolongation unit receiving at least a fraction of said laser pulses of said laser beam from said laser, and using a photoelectric device for converting said at least a fraction of said laser pulses into electrical control signals, said pulse prolongation unit having an intra-cavitary optical element provided within said resonator cavity, for receiving and using said electrical control signals to prolong said laser pulses produced from said resonator cavity of said laser; and
   an intra-cavitary nonlinear crystal provided within said resonator cavity for having said laser beam propagate therethrough to prolong said laser pulses and to generate a second harmonic laser wavelength;
   whereby said pulse prolongation unit and said intra-cavitary nonlinear crystal both contribute to prolongation of a said pulsed to thereby produce pulse durations in a range of $\mu$-seconds.

2. An apparatus according to claim 1, wherein said pulse prolongation unit is activated by light leaving said resonator cavity.

3. An apparatus according to claim 1, wherein said intra-cavitary optical element is a Pockels cell.

4. An apparatus according to claim 1, wherein said intra-cavitary nonlinear crystal raises an optical time constant of said resonator cavity.

5. An apparatus according to claim 1, wherein said intra-cavitary optical element operates both as a Q-switch of said laser and to change the laser pulse form and duration by means of said electrical control signals from said pulse prolongation unit.

6. An apparatus according to claim 1, wherein a Q-switch of said laser is a passive absorber provided in a form of a dye solution.

7. An apparatus according to claim 1, wherein said laser beam has a fundamental wavelength of approximately 750 nm and a pulse energy of up to 300 mJ.

8. An apparatus according to claim 1, wherein an ultra-violet radiation portion of said laser beam has a pulse energy of at least 15 ml at a pump power of 80 mJ per pulse.

9. An apparatus according to claim 1, wherein said resonator cavity of said laser comprises an intra-cavitary deflection mirror such that said resonator cavity is a folded resonator cavity, and further comprises an active medium, wavelength selective and mode-compressing elements and a Q-switch circuit provided between one end mirror of said end mirrors and said intra-cavitary deflection mirror, and said intra-cavitary nonlinear crystal is provided between said intra-cavitary deflection mirror and another end mirror of said end mirrors.

10. An apparatus according to claim 9, wherein said intra-cavitary deflection mirror operates as an exit mirror for said resonator cavity, and is permeable for said second harmonic laser wavelength of said laser beam and reflects a fundamental wavelength of said laser beam.

11. An apparatus according to claim 1, wherein said intra-cavitary nonlinear crystal operates together with said pulse prolongation unit to prolong a duration of an original pulse length of said laser beam by a predetermined factor.

12. An apparatus according to claim 1, wherein said laser is a flashlamp pumped alexandrite laser.

13. An apparatus according to claim 1, wherein said intra-cavitary nonlinear crystal is a BBO crystal.

14. An apparatus according to claim 1, wherein light pulses of said at least one portion of said laser beam are coupled into a quartz fiber and are transmitted by said quartz fiber.

15. An apparatus according to claim 1, wherein said intra-cavitary optical element is a Kerr cell.

16. An apparatus according to claim 1, wherein said intra-cavitary optical element also functions as said Q-switch of said Q-switched solid state laser.

17. An apparatus according to claim 1, further comprising:
   a mode aperture for selection of transversal modes of said laser beam; and
   a tuner for selecting a bandwidth of a fundamental radiation laser beam for outputting from said apparatus.

18. An optical system for generation of laser pulses, said system comprising:
   a Q-switched solid state laser having a Q-switch and end mirror defining a resonator cavity for generation of a laser beam, wherein at least one mirror of said end mirrors is a dielectric mirror through which at least laser pulses of a laser beam are transmitted therethrough to quartz fibers;
   at least one intra-cavitary nonlinear, frequency multiplying crystal provided within said resonator cavity for having said laser beam propagate therethrough to prolong said laser pulses and to generate a frequency-doubled laser beam;
   a pulse prolongation unit receiving at least a faction of said laser pulses of said beam from said laser, and using a photoelectric device for converting said at least a fraction of said laser pulses into electrical control signals, said pulse prolongation unit having an intra-cavitary optical element provided within said resonator cavity, for receiving and using said electrical control signals to prolong said laser pulses produced from said resonator cavity of said laser; and whereby said pulse prolongation unit and said intra-cavitary nonlinear crystal both contribute to prolongation of said laser pulses, and said pulse prolongation unit controls production of said laser pulses developing in said resonator cavity in such a manner that a pulse energy and pulse duration of said laser pulses do not exceed predetermined values which would cause damage to said quartz fibers.

19. An optical system according to claim 18, wherein said frequency-doubled laser beam has a wavelength in an ultraviolet wavelength range, and has pulse energies of at least 15 mJ and pulse durations of at least one $\mu$-second.

20. An optical system according to claim 18, wherein both a fundamental wavelength and a frequency-doubled wavelength of said laser beam emerge from said optical system and are transmitted via said quartz fibers.

21. An apparatus for the generation of laser pulses with pulse durations in a range of $\mu$-seconds, comprising:

a Q-switched solid state laser having a O-switch and end mirrors defining a resonator cavity for generation of a laser beam, wherein at least one mirror of said end mirrors is a semi-reflecting mirror through which at least laser pulses of a laser beam are transmitted therethrough;

a pulse prolongation unit receiving at last a fraction of said laser pulses of said laser beam from said laser, and using a photoelectric device for converting said at least a fraction of said laser pulses into electrical control signals, said pulse prolongation unit having an intra-cavitary optical element provided within said resonator cavity, for receiving using said laser control signals to increase a duration of said laser pulses produced from said resonator cavity of said laser; and an intra-cavitary nonlinear crystal provided within said resonator cavity for having said laser propagate therethrough for generating a second harmonic laser wavelength and contributing to an increase of said duration of said laser pulses.

whereby said pulse prolongation unit and said intro-cavitary nonlinear crystal both contribute to the increase of said duration of said laser pulses to thereby produce pulse durations in a range of $\mu$-seconds.

22. An apparatus for the generation of laser pulses with pulse durations in a range of $\mu$-seconds, comprising:

a Q-switched solid state laser having a O-switch and end mirrors defining a resonator cavity for generation of a laser beam, wherein at least one mirror of said end mirrors is a semi-reflecting mirror through which at least laser pulses of a laser beam are transmitted therethrough;

a pulse prolongation unit receiving at least a fraction of said laser pulses of said laser beam from said laser, and using a photoelectric device for converting said at least a fraction of said laser pulses into electrical control signals, said pulse prolongation unit having an intra-cavitary optical element provided within said resonator cavity, for receiving and using said electrical control signals to increase a duration of said laser pulses produced from said resonator cavity of said laser;

an intra-cavitary nonlinear crystal provided within said resonator cavity for having said laser beam propagate therethrough for generating a second harmonic laser wavelength and contributing to an increase of said duration of said laser pulses; and an intra-cavity deflection mirror disposed within said resonator cavity such that said resonator cavity is a folded resonator cavity, wherein said intra-cavitary deflection mirror operates as an exit mirror for said second harmonic laser wavelength of said laser beam from said resonator cavity and reflects a fundamental wavelength of said laser beam; whereby said pulse prolongation unit and said intra-cavity nonlinear crystal both contributed to the increase of said duration of said laser pulses to thereby produce pulse durations in a range of $\mu$-seconds.

* * * * *